US 8,065,016 B2

(12) United States Patent
Paolini et al.

(10) Patent No.: US 8,065,016 B2
(45) Date of Patent: Nov. 22, 2011

(54) DELAYED STIMULATION IN AUDITORY PROSTHESES

(75) Inventors: Antonio Giacomo Paolini, Bulleen (AU); David Bruce Grayden, Heathmont (AU)

(73) Assignee: The Bionic Ear Institute, Victoria (AU)

( * ) Notice: Subject to any disclaimer, the term of this patent is extended or adjusted under 35 U.S.C. 154(b) by 264 days.

(21) Appl. No.: 10/582,055

(22) PCT Filed: Dec. 8, 2004

(86) PCT No.: PCT/AU2004/001729
§ 371 (c)(1),
(2), (4) Date: May 4, 2007

(87) PCT Pub. No.: WO2005/057983
PCT Pub. Date: Jun. 23, 2005

(65) Prior Publication Data
US 2007/0270949 A1    Nov. 22, 2007

(30) Foreign Application Priority Data
Dec. 10, 2003 (AU) ................................. 2003906846

(51) Int. Cl.
*A61F 2/18* (2006.01)
(52) U.S. Cl. ......................................... 607/57; 607/137
(58) Field of Classification Search .................. 600/377, 600/378; 607/55–57, 137, 2, 3, 45; 623/10
See application file for complete search history.

(56) References Cited

U.S. PATENT DOCUMENTS

| 4,207,441 A | 6/1980 | Ricard et al. | |
| 5,597,380 A * | 1/1997 | McDermott et al. | 607/57 |
| 2001/0031909 A1* | 10/2001 | Faltys et al. | 600/25 |
| 2004/0078057 A1* | 4/2004 | Gibson | 607/3 |
| 2004/0172101 A1* | 9/2004 | Van Hoesel | 607/57 |
| 2005/0033377 A1* | 2/2005 | Milojevic et al. | 607/45 |

FOREIGN PATENT DOCUMENTS

| WO | WO 91/03913 A1 | 3/1991 |
| WO | WO 96/12383 A1 | 4/1996 |
| WO | WO 01/99470 A1 | 12/2001 |
| WO | WO 02/096153 A1 | 11/2002 |
| WO | WO 03/099179 A1 | 12/2003 |

* cited by examiner

*Primary Examiner* — Carl H Layno
*Assistant Examiner* — Allen Porter, Jr.
(74) *Attorney, Agent, or Firm* — McDonnell Boehnen Hulbert & Berghoff LLP

(57) ABSTRACT

A method generating electrical stimuli by an auditory prosthesis (1;1';1") including an array of stimulation devices in response to an incoming acoustic signal, the method including determining stimulation devices to be activated within the array and activation times for those electrodes; and applying a temporal adjustment (12) to the activation times such that activation of electrodes representing lower-amplitude components of the signal is delayed relative to activation of a proximate device representing a higher-amplitude component of the signal.

23 Claims, 3 Drawing Sheets

DELAYED STIMULATION IN AUDITORY PROSTHESES

This application is a National Stage of International Application No. PCT/AU2004/001729, filed Dec. 8, 2004, which claims priority to Australian Patent Application No. 2003906846, filed Dec. 10, 2003.

The present invention relates generally to the generation of electrical stimuli for application by an auditory prosthesis. The invention is suitable for use in the stimulation of cochleas or the auditory brain and it will be convenient to describe the invention in relation to these exemplary, non-limiting applications.

Early signal processing designs for the multi-channel cochlear implant extracted the second formant (F2) and pitch (F0) to control electrode stimulation. The frequency of F2 controlled the location of electrode stimulation, and F0 controlled the rate of stimulation with only one electrode stimulated per pitch period. Improvements were made by also extracting the first formant (F1) and adding a corresponding second stimulated electrode for each pitch period. The MULTIPEAK stimulation strategy, described in U.S. Pat. No. 5,271,397, added stimulation of three fixed electrodes to add high-frequency information. Stimulation times were still controlled by F0 for voiced speech or were random for unvoiced speech.

The Spectral Maxima Sound Processor (SMSP) strategy, described in Australian Patent No. 657,959, and SPEAK strategy, described in U.S. Pat. No. 5,597,380, were a departure from the others as they used a fixed stimulation rate and stimulated electrodes that corresponded to maxima in the sound spectra. Another fixed-rate strategy, CIS, is described in U.S. Pat. No. 4,207,441. This strategy stimulated all of a small number of electrodes to represent the sound spectra. More recently the ACE strategy was developed which is able to perform all of the above strategies. Several stimulation orderings were investigated for the SMSP strategy (Vandali et al. (1995) "Multichannel cochlear implant speech processing: Further variations of the spectral maxima sound processor strategy", Annals of Otology, Rhinology & Laryngology, Supplement 166, Vol. 104, No. 9, Part 2, pp. 378-381): amplitude order, including largest-to-smallest and smallest-to-largest, where the stimulation order for each analysis cycle was controlled by the amplitudes of the maxima; and tonotopic order, where stimulation order was from highest to lowest frequency. The tonotopic ordering scheme showed a small improvement for speech perception in noise. The SPEAK and ACE strategies, by default, all use the tonotopic ordering scheme.

Other recent developments are "A peak-derived timing stimulation strategy for a multi-channel cochlear implant" described in International Patent Application No. WO 02/096153, "Sound processor for a cochlear implant" described in International Patent Application No. WO 01/99470 (called the "Travelling Wave Strategy") and "Generation of electrical stimuli for application to a cochlea" described in International Patent Application No. PCT/AU03/00639 (called "STAR"). These strategies use filters to extract spatio-temporal information about the incoming audio signal and then stimulate the auditory nerve at times based on the properties of the filtered signals. The Travelling Wave Strategy and STAR also introduce travelling wave delays to control timing of excitation.

The auditory brainstem implant is an alternative auditory prosthesis for people and is usually implanted in the cochlear nucleus. An auditory brain implant is a device for stimulation of any area of the auditory system, including the inferior colliculus (midbrain) and auditory cortex. These are generally constructed as a cluster of electrodes in a grid pattern rather than the linear construction of cochlear electrodes. The electrodes are surgically placed in the auditory brain and are stimulated using similar stimulation strategies as cochlear implants, after determining the "place-pitch" equivalents of the implanted electrodes so that assignment of frequencies may be made to the electrodes.

It would be desirable to provide a method and system for generating stimuli for application by an auditory prosthesis array that results in the response of auditory brain neurons more closely resembling the response of a normal hearing listener.

It would also be desirable to provide a method and system for generating stimuli for application by an auditory prosthesis that ameliorates or overcomes one or more disadvantages of known electrical stimuli generation methods and systems.

One aspect of the invention provides a method of generating stimuli by an auditory prosthesis, including an array of stimulation devices, in response to an incoming acoustic signal, the method including:

determining stimulation devices to be activated within the array and activation times for those devices; and applying a temporal adjustment to the activation times such that activation of devices representing lower-amplitude components of the signal is delayed relative to activation of a proximate device representing a higher-amplitude component of the signal.

The auditory prosthesis may be implantable in a cochlea and forms a linear array. Alternatively, the auditory prosthesis may be implantable in an auditory brain and form a grid mapped to the form of a linear array.

The temporal adjustment of the activation times may be determined using delays derived in a manner similar to lateral suppression of amplitude. In the latter, the amplitude of a particular frequency component is reduced by an amount determined by the amplitudes of surrounding components. In the temporal adjustment scheme, the amplitudes of surrounding components instead introduce delays in stimulation of the particular frequency component. This is termed "lateral temporal delay".

The activation time of each stimulation device may be temporally adjusted according to a latency function whereby, for a particular device, a temporal adjustment is applied if the weighted sum of the amplitudes of proximate stimuli exceeds the weighted amplitude of the stimuli be applied by the particular electrode.

In one embodiment, the latency function defines a Mexican-hat shape centred on the stimuli to be applied by the proximate device, with the restriction of being limited to a minimum of no delay.

The latency function $f_x(\vec{x})$ may be defined by:

$$f_x(\vec{x}) = \min\left(0, -2aA_x + a\sum_{\substack{y=1 \\ y \neq x}}^{N} g(y)A_y\right)$$

where $A_x$ is the amplitude of a stimulation to be applied by a stimulation electrode x, a is a scaling factor, N is the number of surrounding filter bands to which the latency function is constrained, and g(y) is a weighting factor to be applied to the amplitude of electrode $A_y$, a stimuli applied by device y.

Where the auditory prostheses requires non-simultaneous stimulation to be applied by the array of stimulation devices, the method may further include:

if there is temporal contention between stimulation to be applied by different devices of the array, discarding one or more lower-amplitude stimuli in favour of a higher-amplitude stimulus.

Where the auditory prostheses requires non-simultaneous stimulation to be applied by the array of stimulation devices, the method may further include:

if there is temporal contention between stimulation to be applied by different devices of the array, applying a further temporal delay to one or more lower-amplitude stimuli by one or more stimulation slots in favour of a higher-amplitude stimulus.

In one embodiment of the invention, the array of stimulation devices includes one or more electrodes, each electrode being activated by the application of a stimulation pulse.

In another embodiment, the array of stimulation devices includes one or more drug delivery units for the delivery of drugs to a user at predetermined locations. The drug delivery units may be realised as fluidic microchannels.

Another aspect of the invention provides a system for generating stimuli for application by an auditory prosthesis including an array of stimulation devices, the system including:

a stimulator unit for selectively activating stimulation devices in the array; and a processor for processing received sound signals and controlling the operation of the stimulator unit by carrying out a method as described above.

In embodiments of the invention where the stimulation devices are electrodes, the stimulator unit may act to activate the one or more electrodes by selectively applying stimulation pulses to the electrodes.

In embodiments of the invention where the stimulation devices are drug delivery units, the stimulator unit may include a drug storage device and a drug delivery pump for delivering drugs stored in the drug storage device through the drug delivery units to a user.

A further aspect of the invention provides a processor for use in a system for generating stimuli for application by an auditory prosthesis including an array of stimulation devices, the system including a stimulator unit for selectively activating stimulation devices in the array, the processor including digital signal processing means for processing received sound signals and controlling the operation of the stimulator unit by carrying out a method as described above.

Neurophysiological recordings suggest that the cochlear nucleus, the first stage of auditory processing in the brainstem, converts frequency information to timing information in a dynamic fashion where frequencies of interest are processed faster than less relevant information. This is achieved through interactions of inhibition and excitation. The frequencies of interest are those whose amplitude is greater than surrounding frequencies. The present invention generates stimuli for application to a cochlea, auditory brainstem or other region of the auditory brain via an auditory prosthesis where the timing of stimulation can be modified by a latency model based on physiological data obtained from extra- and intra-cellular recordings in the ventral cochlear nuclei. The excitation of cochlear implant or auditory brain implant stimulation devices is delayed for lower-amplitude frequency bands relative to their neighbouring higher-amplitude frequency bands.

The general sound processing strategy to which the invention can be applied may be any strategy currently implemented or proposed for cochlear implant or auditory brain implant stimulation. These strategies will hitherto be referred to as the "base" strategies. In particular, strategies that stimulate electrodes at precise times based on the properties of the incoming acoustic signal would be preferred. These include, but are not limited to, the Peak-Derived Timing Stimulation strategy, the Travelling Wave strategy and the STAR strategy.

The invention provides a method for processing the stimulation sequences resulting from existing sound processing strategies to generate stimuli for application by an auditory prosthesis including an array of stimulation devices, the method entailing the introduction of delay in stimulation time for devices depending on their stimulation amplitude compared to the stimulation amplitude proximate devices. The time of activation of a stimulation device is obtained from the time normally used by the base stimulation strategy and a latency function.

Physiological data show that if a delay is introduced (irrespective of that already introduced to compensate for travelling wave) to frequencies which are not important then information of importance such as formants in speech or signals in noise will be sent to brain sooner and this will aid in their identification and improve speech recognition. This delay may be particularly important for speech perception in noise as the neural elements involved in this processing respond best to noise. A mechanism also exists to enhance this delay further through bilateral inhibitory connections between cochlear nuclei.

The ventral cochlear nucleus (VCN) stellate population has been divided into T and D Stellate cells. D Stellate cells are inhibitory and known to project to T Stellate neurons, which are excitatory. Intracellular in vivo studies in the VCN demonstrate that D Stellate neurons display a significantly shorter latency to initial depolarisation than T Stellate cells, which is also reflected in shorter first-spike latency. Whereas prolonged inhibition can reduce spike regularity in T stellate neurons, given the morphological organisation of D and T stellate cells, the data provides compelling evidence that, for a tone at a given frequency, fast duration inhibitory input from D Stellate cells may delay the onset of firing of T Stellate cells with CF's below or above that of the tone depending on its intensity. This implies that the timing of action potential generation may be related to the frequency of presentation. For a given frequency then, D stellate cells delay the firing of neighbouring T stellate cells located in different iso-frequency laminae providing a timing que for frequency identification.

The D Stellate cells' inhibition is fast both in duration (<10 ms) and synaptic delay (~0.3 ms) and is most responsive to broadband stimuli. It may play a crucial role in establishing appropriate neural delays without the need for anatomically arranged delay lines. As inhibition via D stellate cells is more likely to be activated in noise and if, as proposed, inhibition plays a role in maintaining regular chopping behaviour in T Stellate cells, the timing and interplay of excitation and inhibition may be particularly crucial for signal detection in noisy environments. This has implications not only for signal detection in noise but also for coding as a whole and may circumvent the need for and provide a more dynamic organisation than anatomically arranged delay lines in the coding of monaural and binaural information.

In a normal hearing person's auditory pathway, the inhibitory connections may be performing this role. However, auditory brain implants bypass the auditory nerve and thereby remove the possibility of this processing taking place. Therefore, it is believed that introducing the control of latency of stimulation will restore this behaviour to the auditory brain.

In addition, there is evidence that the inhibitory pathways in the hearing impaired person are compromised because of lack of auditory input for some time. Therefore, the strategy may improve cochlear implant users' speech perception, especially in the presence of noise.

The following description refers in more detail to the various features of the method and system for generating stimuli of the present invention. To facilitate an understanding of the invention, reference is made in the description to the accompanying drawings where the invention is illustrated in a preferred embodiment. It is to be understood however, that the invention is not limited to the preferred embodiment as shown in the drawings.

Figure 1:
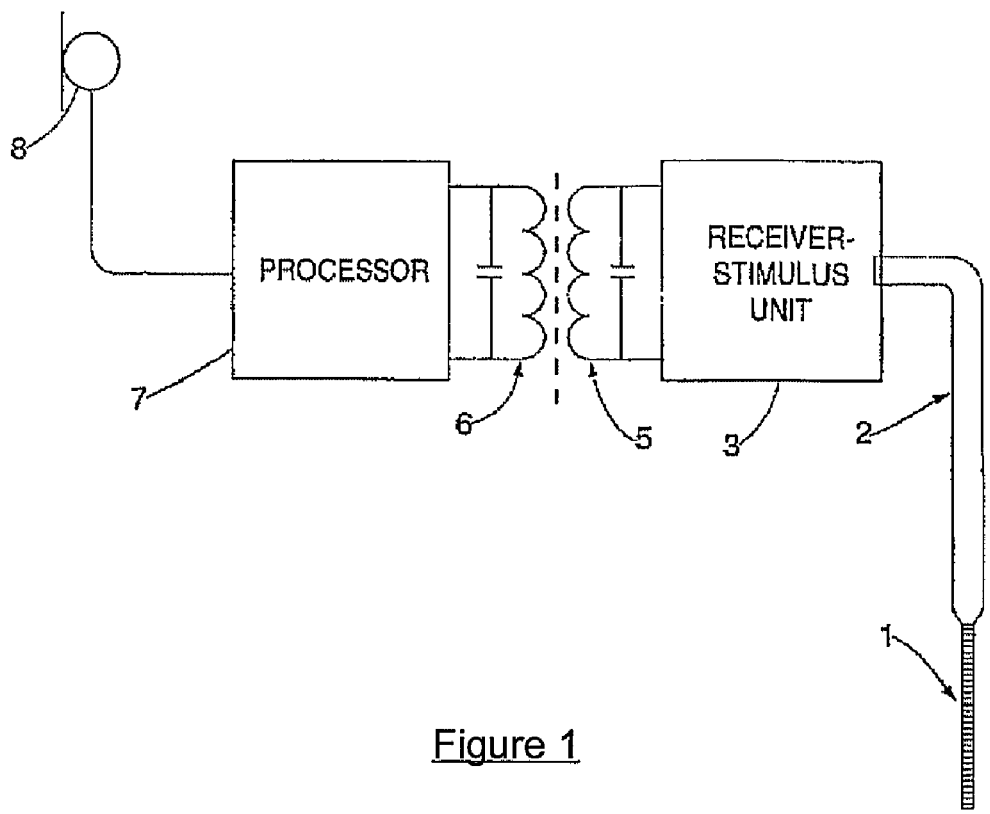
FIG. 1 is a schematic diagram of a first embodiment of a system for stimulating an electrode array implanted into a cochlea.

Referring now to FIG. 1, there is shown generally a system for generating stimuli for application by an auditory prosthesis, including an array of stimulation devices, in response to a processed signal. In this embodiment, an electrode array 1 for implanting into a cochlea connects via cable 2 to a receiver-stimulator unit (RSU) 3. The physical form of the electrode array may be different to that shown in the figure and depends on the device and location of implantation. The implanted system receives control signals and power from an external speech processor unit, preferably via a tuned coil RF system 5, 6 as illustrated. However, any alternative connection technique such as percutaneous connection may be employed or a fully implantable device may be used that does not require transmission through the skin.

The coil 6 carries a signal modulated by the processor 7 so as to cause the RSU 3 to activate the electrodes in the electrode array by applying stimulation pulses in a desired sequence, timing and amplitude. The processor 7 in turn receives electrical analog signals from a microphone 8 worn by, or implanted in, the user. The present invention is concerned with the operation of the processor and particularly the method of post-processing the stimulation sequence for activating the electrodes.

Figure 2:
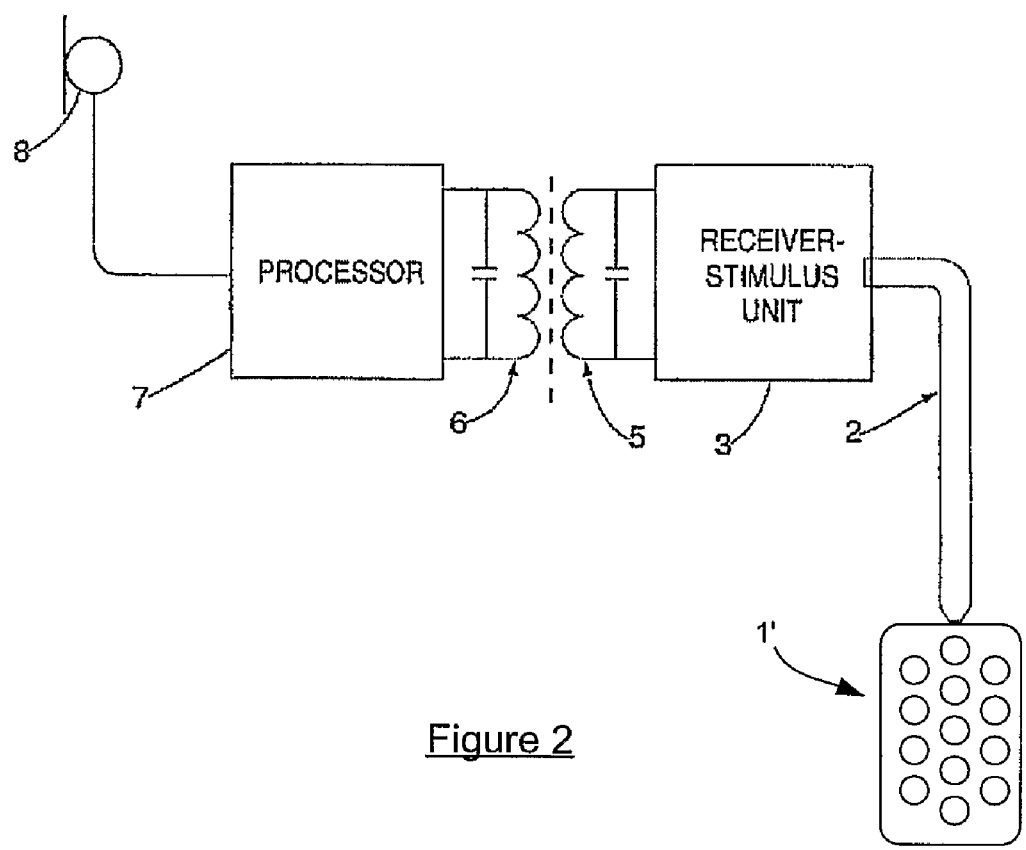
FIG. 2 is a schematic diagram of a second embodiment of a system for stimulating an electrode array implanted into an auditory brain.

FIG. 2 shows a variation to the system shown in FIG. 1 in which the electrode array 1' forms part of an auditory brain implant that bypasses the cochlea altogether. The electrode array 1' is attached directly to the auditory brain at the base of the brain or some position higher up in the auditory pathway. The electrode array 1' forms a grid mapped to the form a linear electrode array.

Figure 3:
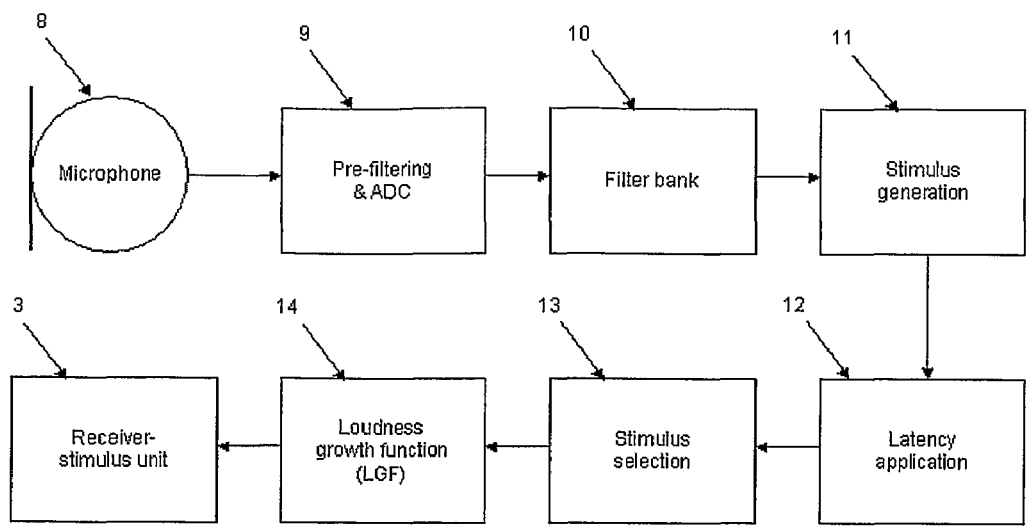
FIG. 3 is a schematic diagram showing the function blocks of a processor. forming part of the electrode stimulation systems shown in FIGS. 1 and 2.

FIG. 3 illustrates the various functional blocks of the processor 7, including a pre-filtering & ADC block 9, a filter bank 10, a stimulus generation block 11, a timing latency block 12, a stimulation selection & ordering block 13 and a loudness growth function block 14. The pre-filtering & ADC block 9 may be implemented using known electronic circuitry and analog signal sampling techniques, whilst the functional blocks 10 to 14 may be implemented using known digital signal processing techniques.

Base Sound Processing

Sound is recorded by the microphone 8, which may inherently apply pre-emphasis to the incoming signal. This signal is low-pass filtered, to prevent aliasing during sampling, and is then sampled by an analog-to-digital converter in the pre-filtering and ADC block 9. The base sound processing is then performed on the signal that divides it up into a number of channels representing different frequencies 10. In an embodiment of the invention using the CI-24M cochlear implant, up to 22 channels may be used. The base sound processing system then determines the electrodes to be activated by application of stimulation pulses, and its own determination of the times that this activation should take place 11. For the Peak-Derived Timing Stimulation strategy, these are the times that each filtered waveform reaches a peak between zero crossings; for the Travelling Wave and STAR strategies, these are the times extracted from the rectified or threshold-crossing times of each filtered waveform plus the travelling wave delay introduced for each electrode. Other base stimulation strategies have their own method of generating the stimulation times.

Introduction of Amplitude-based Excitation Time Latency

Figure 4:
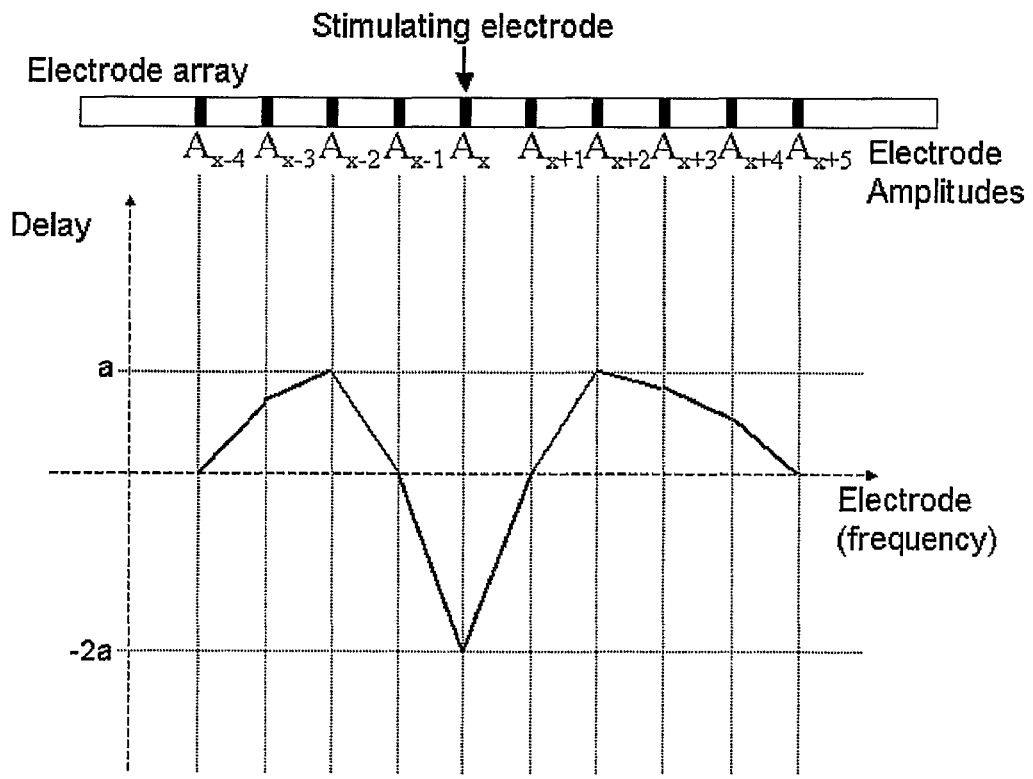
FIG. 4 is an exemplary form of the latency function used to determine the amount of delay to be introduced for a particular electrode of the electrode stimulation system shown in FIGS. 1 and 2.

Additional latency is introduced based on the amplitude of a filter band relative to the amplitudes of neighbouring filter bands in the filter bank 10. The function displayed in FIG. 4 illustrates a possible form of the latency function utilising lateral temporal delay. This works in a manner similar to traditional lateral suppression, where the amplitudes of proximate frequency components suppress the amplitude of the filter band, except that instead of changing amplitudes of outputs, the timing of outputs is adjusted. Accordingly, the temporal adjustment applied to the activation time of each electrode is derived from the amplitudes of stimuli to be applied by proximate electrodes. In this figure, the stimulating electrode represents an electrode which will be activated by application of a stimulus current pulse.

The time of activation of the electrodes proximate to the stimulating electrode is determined by the following formula:

$$T_x = T_{base}(x) + f_x(\vec{x})$$

where $T_x$ is the time to stimulate electrode x, $T_{base}(x)$ is the base strategy's activation time for electrode x and $f_x(\vec{x})$ is the temporal delay caused by the relationship of the amplitude of this filter band to the surrounding filter bands for other electrodes.

The latency function $f_x(\vec{x})$ defines a Mexican-hat shape centered on the stimuli to be applied by the proximate electrode, with the further restriction that it be limited to a minimum of zero, or no delay. A delay will be introduced if the weighted sum of the amplitudes of the filter bands for surrounding electrodes exceeds the value of the current electrode's amplitude. For an electrode that is a local maximum, the weighted sum will be negative and so no extra delay will be added. However, if there is a nearby electrode or group of electrodes with greater amplitude, then the activation time will be delayed. The formula for $f_x(\vec{x})$ is of the form $$f_x(\vec{x}) = \min\left(0, -2aA_x + a\sum_{\substack{y=1 \\ y \neq x}}^{N} g(y)A_y\right)$$

where $A_x$ is the amplitude of a stimulation to be applied by stimulation electrode x, a is a scaling factor, N is the number of surrounding filter bands to which the latency function is constrained, and g(y) is a weighting factor to be applied to the amplitude of electrode $A_y$, as illustrated in FIG. 4. The latency function may be constrained to a limited number of electrodes only in the electrode array or may include all electrodes in the array. The actual value of N may vary according to the listener, the auditory prosthesis and the aural environment in question.

The electrode array 1 shown in FIG. 1 typically includes 22 electrodes, however the latency function is constrained to a limited number of electrodes proximate the electrode to which a high-amplitude stimuli is to be applied. In the example shown in FIG. 4, the latency function is constrained to apply to 4 electrodes at lower frequencies and five electrodes at higher frequencies (although four of these make no contribution). It will be appreciated that FIG. 4 represents an exemplary subset of electrodes in a typical cochlear implant or auditory brain implant. Multi-electrode implants currently include from 4 to 22 electrodes although in future designs even more electrodes may be included. The invention may be applied to multi-electrode implants including any number of electrodes.

Moreover, different extents and shapes of latency functions may be used in other embodiments of the invention, including different frequency extents on the low and high frequency sides and this may vary for different stimulating electrodes. It is to be understood that the latency function described above is merely one possible form of a latency function suitable for use with the present invention, and that other functions may be envisaged by a skilled addressee that cause the stimulation of electrodes representing lower-amplitude components of the signal to be delayed relative to stimulation of a proximate electrode representing a higher-amplitude component of the signal.

A scheme for auditory brain implant processing is similar to that described above and illustrated in FIG. 4. The electrodes are not usually in a linear configuration, so the scheme operates by using the frequencies that are assigned in the method usually prescribed for auditory brain prostheses and mapped to the form of the electrode array illustrated in FIG. 4.

Further Processing

After the introduction of latency to electrode stimulation time, control passes back to the base stimulation strategy. It is at this stage that electrode selection and ordering must take place to determine which electrodes will be activated over the coming time interval and to deal with issues of contention where the activation times for two or more electrodes may be the same in the stimulus selection and ordering block 13. Implants are limited in the number of stimuli that may be provided per second, so electrode selection is required to ensure that this limit is observed. The procedure for doing this is usually to choose those electrodes with the largest amplitude of stimulation, but this is dependent on the base strategy and the prosthesis that is being used.

Most current implants require that activation of multiple electrodes be non-simultaneous. It is for this reason that contention may be considered. This is also dependent on the base strategy, but where the base strategy does not consider this possibility, low amplitude stimuli may be discarded or delayed further in preference for higher amplitude stimuli. The stimulation provided by an auditory prosthesis that requires non-simultaneous activation may be divided into stimulation slots, where there is one slot for each activation time permitted. For example, the CI-24M implant, which has a maximum stimulation rate of 14,400 pulses per second, has 14,400 stimulation slots per second. Stimuli are assigned to these stimulation slots by the base strategy. The extra delay to be introduced to overcome electrode contention may be performed by shifting the lower amplitude stimuli into the next slot. Then the next slot is considered and if multiple stimuli are in that slot, then the lower amplitude stimuli are shifted to the next slot. This procedure continues for each stimulation slot. If a stimulus has been postponed for more than a reasonable amount of time, then it will be discarded to avoid extraneous stimulation. This time could be around 0.5 msec (corresponding to about 22 stimulation slots for the CI-24M) although it may vary for different electrodes and different implementations.

After each cycle of electrode selection, the stimuli are mapped to current levels using the standard loudness growth function (LGF) and the stored map (T and C levels) for the user by the loudness growth function block 14. The LGF is a logarithmic function relating stimulus level to loudness to obtain an appropriate increase in subjective loudness. The stored map specifies the minimum and maximum current levels permitted for a user. This is, again, a property of the implant and base strategy.

The stimulus sequence is then transmitted to the receiver-stimulus unit 3 that interfaces with the auditory prosthesis and encodes the electrode selection and current level information to the device.

An alternative auditory prosthesis to which the present invention is able to be applied is a drug delivery neural implant array. This is a new form of implant that uses drug delivery arrays that can establish chemical interfaces with neurons. These arrays may also include electrodes for the activation of neurons by electrical current. Arrays that include both drug delivery devices and electrical stimulation devices are called hybrid neural implant systems. Drug delivery arrays selectively release drugs through drug delivery units, such as fluidic microchannels that activate receptors on discrete clusters of neural elements to stimulate neural activity. The delivery of drugs acts to alter the membrane potential of neurons and thereby excite or inhibit local neurons. An advantage of using drug delivery for neural stimulation is that an array will not stimulate the fibres of passage or activate back-propagation in neurons.

Figure 5:
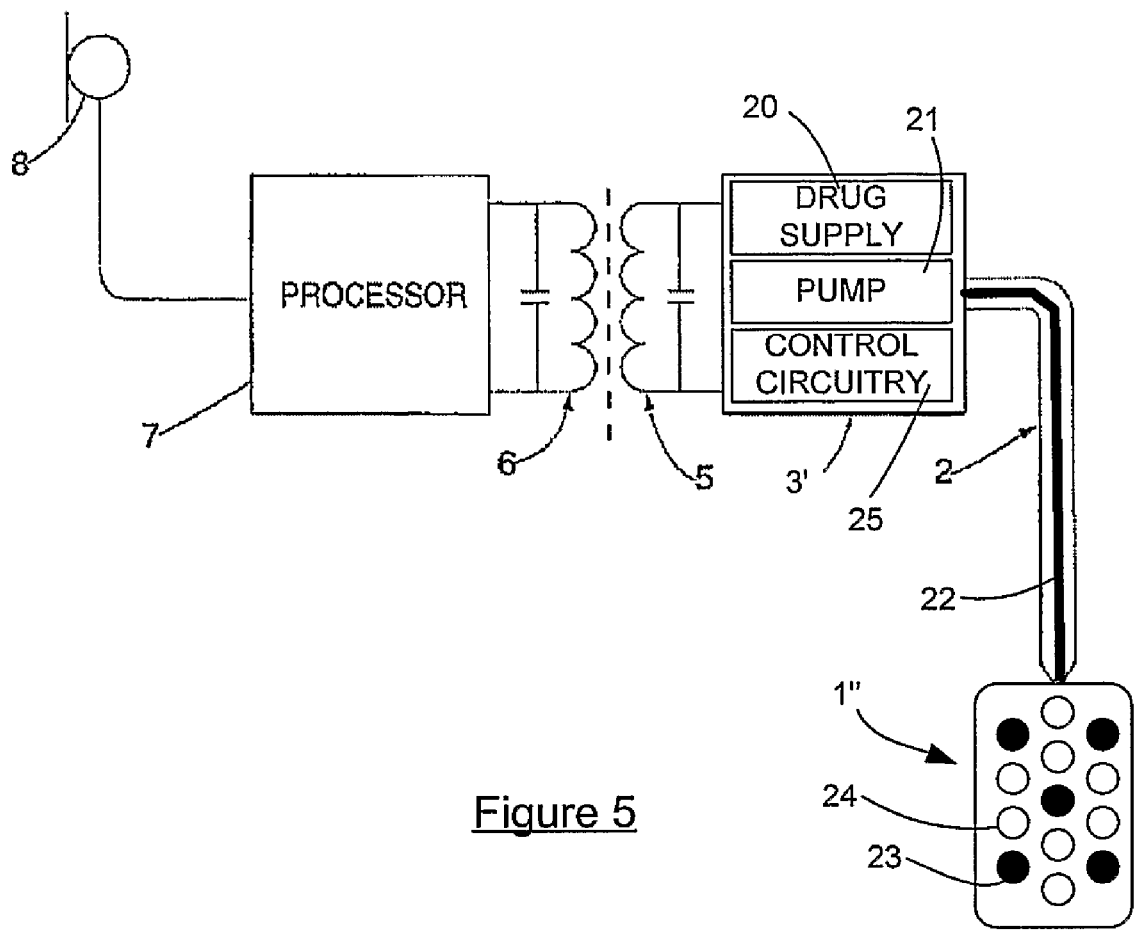
FIG. 5 is a schematic diagram of an embodiment of a system for selectively releasing drugs in an array of drug delivery units and stimulating an electrode array implanted into a cochlea.

FIG. 5 shows an embodiment of a system for generating stimuli for application by an auditory prosthesis, including an array of stimulation devices, in response to a processed signal that is similar to the auditory prosthesis stimulation systems shown in FIGS. 1 and 2. In this embodiment however, the receiver-stimulus unit 3—includes a drug supply 20 and pump 21 for delivering drugs stored in the drug supply device 20 to the usr via fluidic microchannels 22 running within the cable 2. The ends (the dark dots, an exemplary one of which is referenced 23) of the fluidic microchannels form part of a hybrid array 1—for stimulating the auditory brain. The hybrid array 1—also includes electrodes (clear dots, an exemplary one of which is referenced 24) that are selectively activated by application of stimulation pulses via control circuitry 25 forming part of the receiver-stimulus unit 3-. In this case, the amplitude of the stimuli applied by the fluidic microchannels corresponds to the quantity of drugs delivered by each fluidic microchannel, whereas the amplitude of the stimulator applied by electrodes is determined by the amplitude of the electrical stimulation pulse applied to each electrode. The previously described method of generating stimuli for each stimulation device within the hybrid array 1—conforms to the method previously described in relation to the embodiments of the invention shown in FIGS. 1 and 2.

It is to be understood that various modifications and/or additions may be made to the method for modifying the latency of electrical stimuli described herein without departing from the spirit or ambit of the present invention. For example, in other embodiments of the invention, it is possible that the array of stimulation devices includes only drug delivery units so that stimulation of the auditory brain occurs only by means of the application of drugs without separate electrical stimulation.

The invention claimed is:

1. A method for generating stimuli by an auditory prosthesis, including an array of stimulation electrodes, in response to an incoming acoustic signal, the method including:
   (a) dividing the incoming acoustic signal to obtain a plurality of filter band signals, each filter band corresponding to a stimulation electrode to be activated within the array and determining activation times for those stimulation electrodes;
   (b) deriving temporal adjustments for each stimulation electrode using a latency function, wherein for a particular stimulation electrode, the latency function depends on filter band signal amplitudes of a plurality of surrounding filter bands, and the latency function is constrained by a predetermined frequency range of the plurality of surrounding filter bands, relative to the filter band frequency of the particular stimulation electrode;
   (c) applying the temporal adjustments to the activation times of the stimulation electrodes, such that activation of stimulation electrodes corresponding to lower-amplitude filter band signals of said predetermined frequency range are delayed relative to activation of stimulation electrodes corresponding to higher-amplitude filter band signals of said predetermined frequency range; and
   (d) generating a stimulus using one or more of the stimulation electrodes.

2. A method according to claim 1, wherein the auditory prosthesis is implantable in a cochlea and forms a linear array.

3. A method according to claim 1, wherein the auditory prosthesis stimulation electrode array is implantable in an auditory brain and forms a grid mapped to the form of a linear array.

4. A method according to claim 1, wherein the latency function for a particular stimulation electrode includes a weighted sum of the amplitudes of a plurality of surrounding filter band signal amplitudes and a temporal adjustment is made if said weighted sum exceeds the an amplitude of the stimuli to be applied by the particular stimulation electrode.

5. A method according to claim 4, wherein the latency function $f_x(\overline{x})$ is defined by:

$$f_x(\vec{x}) = \min\left(0, -2aA_x + a\sum_{\substack{y=1 \\ y \neq x}}^{N} g(y)A_y\right)$$

where $A_x$ is the amplitude of a stimulation to be applied by stimulation electrode x, a is a scaling factor, N is the number of surrounding filter bands to which the latency function is constrained, and g(y) is a weighting factor to be applied to the amplitude of stimulation to be applied by stimulation electrode $A_y$.

6. A method according to claim 1, wherein the stimulation electrode array of the auditory prostheses requires non-simultaneous stimulation to be applied by the array of stimulation electrodes, the method further including:
   if there is temporal contention between stimulation to be applied by different electrodes of the array, discarding one or more lower-amplitude stimuli in favor of a higher-amplitude stimulus.

7. A method according to claim 1, wherein the auditory prostheses requires non-simultaneous stimulation to be applied by the array of stimulation electrodes, the method further including:
   if there is temporal contention between stimulation to be applied by different stimulation electrodes of the array, applying a further temporal delay to one or more lower-amplitude stimuli by one or more stimulation slots in favor of a higher-amplitude stimulus.

8. A method according to claim 1, wherein the auditory prosthesis includes one or more drug delivery units for delivering drugs to a user at predetermined locations.

9. A method according to claim 8, wherein the drug delivery units are fluidic microchannels.

10. A system for generating stimuli in response to an incoming acoustic signal for application by an auditory prosthesis including an array of stimulation electrodes, including:
    a stimulator unit for selectively activating stimulation electrodes in the array; and
    a processor for processing received sound signals and controlling the operation of the stimulator unit using a method including:
    (a) dividing the incoming acoustic signal to obtain a plurality of filter band signals, each filter band corresponding to a stimulation electrode to be activated within the array; and determining activation times for those stimulation electrodes; and
    (b) deriving temporal adjustments for each stimulation electrode using a latency function, wherein for a particular stimulation electrode, the latency function depends on the filter band signal amplitudes of a plurality of surrounding filter bands, and the latency function is constrained by a predetermined frequency range of surrounding filter bands, relative to the filter band frequency of the particular stimulation electrode;
    (c) applying the temporal adjustments to the activation times of the stimulation electrodes, such that activation of stimulation electrodes corresponding to lower-amplitude filter band signals of said predetermined frequency range are delayed relative to activation of stimulation electrodes corresponding to higher-amplitude filter band signals of said predetermined frequency range.

11. A system for generating stimuli for application by an auditory prosthesis as claimed in claim 10 wherein the latency function for a particular stimulation electrode includes a weighted sum of the amplitudes of a plurality of surrounding filter bands and a temporal adjustment is made if said weighted sum exceeds the weighted amplitude of the stimuli to be applied by the particular stimulation electrode.

12. A system for generating stimuli for application by an auditory prosthesis as claimed in claim 11, wherein the latency function $f_x(\overline{x})$ is defined by:

$$f_x(\vec{x}) = \min\left(0, -2aA_x + a\sum_{\substack{y=1 \\ y \neq x}}^{N} g(y)A_y\right)$$

where $A_x$ is the amplitude of a stimulation to be applied by a stimulation electrode x, a is a scaling factor, N is the number of surrounding filter bands to which the latency function is constrained, and g(y) is a weighting factor to be applied to the amplitude of electrode $A_y$.

13. A system for generating stimuli for application by an auditory prosthesis as claimed in claim 10, wherein the stimulation electrode array of the auditory prostheses requires non-simultaneous stimulation to be applied by the array of stimulation electrodes, and wherein the processor is further configured to discard one or more lower-amplitude stimuli in favor of a higher-amplitude stimulus, in the event that there is temporal contention between stimulation to be applied by different electrodes of the array.

14. A system for generating stimuli for application by an auditory prosthesis as claimed in claim 10, wherein the auditory prostheses requires non-simultaneous stimulation to be applied by the array of stimulation electrodes, and the processor is further configured to apply a further temporal delay to one or more lower-amplitude stimuli by one or more stimulation slots in favor of a higher-amplitude stimulus, in the event that there is temporal contention between stimulation to be applied by different stimulation electrode of the array.

15. A system for generating stimuli for application by an auditory prosthesis as claimed in claim 10 wherein the array of stimulation electrodes includes one or more drug delivery units for the delivery of drugs to a user at predetermined locations.

16. A system according to claim 15 wherein the stimulator unit includes a drug storage device and a drug delivery pump for delivering drugs stored in the drug storage device through the drug delivery units to a user.

17. A system for generating stimuli for application by an auditory prosthesis as claimed in claim 10 wherein the auditory prosthesis is implantable in a cochlea and forms a linear array.

18. A system for generating stimuli for application by an auditory prosthesis as claimed in claim 10 wherein the auditory prosthesis stimulation electrode array is implantable in an auditory brain and forms a grid mapped to the form of a linear array.

19. A system for generating stimuli for application by an auditory prosthesis as claimed in claim 10 wherein the processor is further configured to apply the temporal adjustment to the activation time of stimulation electrode derived from the amplitudes of stimuli to be applied by proximate stimulation electrodes.

20. A system for generating stimuli for applications by an auditory prosthesis as claimed in claim 10, wherein the stimulator unit acts to activate the one or more electrodes by selectively applying stimulation pulses to the electrodes.

21. A processor for use in a system for generating stimuli in response to an incoming acoustic signal for application by an auditory prosthesis including an array of stimulation electrodes, the system including a stimulator unit for selectively activating stimulation electrodes in the stimulation electrode array, the processor configured to:
  (a) divide the incoming acoustic signal to obtain a plurality of filter band signals, each filter band corresponding to a stimulation electrode to be activated within the array; and determining activation times for those stimulation electrodes; and
  (b) derive temporal adjustments for each stimulation electrode using a latency function, wherein for a particular stimulation electrode, the latency function depends on the filter band signal amplitudes of a plurality of surrounding filter bands, and the latency function is constrained by a predetermined frequency range of surrounding filter bands, relative to the filter band frequency of the particular stimulation electrode;
  (c) applying the temporal adjustments to the activation times of the stimulation electrodes, such that activation of stimulation electrodes corresponding to lower-amplitude filter band signals of said predetermined frequency range are delayed relative to activation of stimulation electrodes corresponding to higher-amplitude filter band signals of said predetermined frequency range.

22. A processor for use in a system for generating stimuli for application by an auditory prosthesis as claimed in claim 21, wherein the processor is further configured to discard one or more lower-amplitude stimuli in favor of a higher-amplitude stimulus, in the event that there is temporal contention between stimulation to be applied by different stimulation electrode of the array.

23. A processor for use in a system for generating stimuli for application by an auditory prosthesis as claimed in claim 21, wherein the processor is further configured to apply a further temporal delay to one or more lower-amplitude stimuli by one or more stimulation slots in favor of a higher-amplitude stimulus, in the event that there is temporal contention between stimulation to be applied by different stimulation electrode of the array.

* * * * *